US006414119B1

(12) United States Patent
Fisher (10) Patent No.: US 6,414,119 B1
(45) Date of Patent: Jul. 2, 2002

(54) RAPIDLY GREENING, LOW OXYGEN MUTANT OF THE AEQUORIA VICTORIA GREEN FLUORESCENT PROTEIN

(75) Inventor: Hugh Fisher, North Brunswick, NJ (US)

(73) Assignee: Rutgers, the State University, New Brunswick, NJ (US)

( * ) Notice: Subject to any disclaimer, the term of this patent is extended or adjusted under 35 U.S.C. 154(b) by 0 days.

(21) Appl. No.: 09/418,785

(22) Filed: Oct. 15, 1999

Related U.S. Application Data (60) Provisional application No. 60/104,563, filed on Oct. 16, 1998.

(51) Int. Cl.[7] .......................... C07K 14/435; C12N 9/02
(52) U.S. Cl. ....................................... 530/350; 435/189
(58) Field of Search ........................... 435/189; 530/350

(56) References Cited

PUBLICATIONS

R. Heim, et al. Wavelength Mutations and Posttranslational Autoxidation of Green Fluorescent Protein. (1994) *Proc. Natl. Acad. Sci.* 91:12501–12504.
R. Heim, et al. Improved Green Fluorescence. (1995) *Nature* 373:663–664.
B.P. Cormack, et al. FACS–Optimized Mutants of the Green Fluorescent Protein (GFP). (1996) *Gene* 173:33–38.
A. Crameri, et al. Improved Green Fluorescent Protein by Molecular Evolution Using DNA Shuffling. (1996) *Nature Biotechnology*. 14:315–319.
S. Delagrave, et al. Red–Shifted Excitation Mutants of the Green Fluorescent Protein. (1995) *Bio/technology*. 12:151–154.
B.G. Reid and G.C. Flynn. Chromophore Formation in Green Fluorescent Protein. (1997) *Biochemistry*. 36:6786–6791.
F. Yang, et al. The Molecular Structure of Green Fluorescent Protein. (1996) *Nature Biotechnology*. 14:1246–1251.
M. Ormo, et al. Crystal Structure of the Aequorea Victoria Green Fluorescent Protein. (1996) *Science*. 273:1392–1395.
W. Ward. *Biochemical and Physical Properties of Green Fluorescence Protein*. 1998. 45–75. In *Green Fluorescent Protein: Properties, Applications and Protocols*, M. Chalfie and S. Kain, eds., Willey–Liss.
Palm et al. (May 1997) Nature Structural Biology, vol. 4(5), pp. 361–365.*

* cited by examiner

*Primary Examiner*—Elizabeth Slobodyansky
(74) *Attorney, Agent, or Firm*—Licata & Tyrrell P.C.

(57) ABSTRACT

A novel catagory of Green Fluorescent Protein (GFP) is disclosed, which exhibits the novel trait of rapid chromophore formation under reduced oxygen levels while maintaining a fluorescence spectrum similar to the wildtype GFP. Examples of this category of low oxygen variants are the mutations F64C, F64M and V68C. These GFP variants also exhibit the useful traits of thermotolerance and higher fluorescence yield. Mutants that combine this low oxygen chromophore development with mutations conferring blue or red fluorescence are also disclosed. These fluorescent proteins may be used in any of the applications where the wild type green fluorescent protein is used, as well as many new anaerobic applications where GFP could previously not be used.

8 Claims, 7 Drawing Sheets

Nucleotide sequence changes:

| 64 | 65 | 66 | |
|---|---|---|---|
| ttc | tct | tat | wildtype |
| tgc | tct | tat | F64C mutant (NSS#1) |
| ttc | tct | cat | Y66H mutant |
| ttc | act | tat | S65T mutant |
| tgc | tct | cat | F64C Y66H double mutant (NSS(blue)) |
| tgc | act | tat | F64C S65T double mutant (NSST) |

RAPIDLY GREENING, LOW OXYGEN MUTANT OF THE AEQUORIA VICTORIA GREEN FLUORESCENT PROTEIN

This application claims priority to U.S. 60/104,563, filed Oct. 16, 1998, the entirety of which is incorporated by reference herein.

FIELD OF THE INVENTION

This invention relates to the field of biotechnology research products, fluorescent proteins and microscopy.

BACKGROUND OF THE INVENTION

Various scientific articles are referred to in parentheses throughout the specification. These articles are incorporated by reference herein to describe the state of the art to which this invention pertains.

The green fluorescent proteins (GFPs) are a unique class of chromoproteins found in many bioluminescent hydrozoan and anthozoan coelenterates, including the hydromedusan jellyfish (*Aequoria victoria*). The gene for *A. victoria* GFP has been cloned into procaryotic and eucaryotic hosts and is expressed in such organisms as a functional fluorescent protein with spectral characteristics identical to the native *A. victoria* GFP.

Mutants of *A. victoria* GFP with altered spectral properties have been isolated or created. For instance, a $Tyr_{66}$ His mutant (Heim et al., Proc. Natl. Acad. Sci. USA 91: 12501–12504, 1994) displays blue fluorescence instead of green, and a $Ser_{65}$ Thr mutant (Heim et al., Nature 373: 663–664, 1994) displays a red-shifted absorption peak. A set of mutants within and surrounding the chromophore has been disclosed (Cormack et al., Gene 173: 33–38, 1996), which have shifted excitation spectra and possible improved folding properties, as compared with wild-type GFP.

In nature, GFP from *A. victoria* converts would-be blue bioluminescence from excited aequorin to green (λmax=509), identical in color to its own fluorescence. The GFP chromophore is formed by post-translational cyclization of an internal peptide, Ser65-deHTyr-Gly. Though the chemical mechanism for chromophore formation is not fully understood, it is clear that molecular oxygen is required. It also appears that chromophore formation is an autocatalytic event, requiring no cofactors or enzymes other than the GFP itself.

Chromophore formation in GFP is relatively slow, occurring with a time constant of approximately 4 hours. Variants have been created or selected in *E. coli* with post-translational chromophore formation rates of less than two hours. For instance, the "cycle 3" variant (Crameri et al., Nature Biotech. 14: 315, 319, 1996), reaches 50% of maximum fluorescence in *E. coli* in 95 minutes following induction of expression. However, chromophore formation even in this mutant is dependent on the presence of molecular oxygen. In low oxygen, chromophore formation is retarded, as is the case with wild-type GFP.

The requirement for molecular oxygen for chromophore formation in GFP limits the utility of cloned GFP and GFP mutants for bioluminescent labeling under low-oxygen conditions, such as often exist in cells or tissues in situ and in vivo. The use of GFP is also limited to the range of environmental conditions in which wild type GFP is stable. Accordingly, a need exists to create or select for GFP mutants capable of chromophore formation in low oxygen and with increased stability.

SUMMARY OF THE INVENTION

In accordance with the invention, a new category of green fluorescent protein variant is provided. Several single amino acid changes around the chromophore of the protein are described that give the GFP the novel characteristic of rapid chromophore formation under low oxygen conditions as examples of this new category. This category of variant also has the benefits of rapid chromophore formation under conditions of normal oxygen and surprising stability.

One aspect of the invention is a new category of GFP variant in which the chromophore forms at low it oxygen concentrations. In a preferred embodiment, this GFP variant also has more rapid chromophore formation than the wild type GFP at normal oxygen conditions. In a most preferred embodiment, the variant is also more thermotolerant than the wildtype GFP.

Another aspect of the invention is a variant in GFP protein that comprises a native GFP protein with at least one mutation, where the mutation is selected from F64C, F64M and V68C; and the GFP protein is at least 80% similar to SEQ ID NO:1. In a preferred embodiment, the variant protein additionally has a mutation selected from Y66H and S65T. This embodiment also include antibodies immunologically specific to peptides comprising the variant amino acids at positions 64 or 68.

Another aspect of the invention encompasses nucleic acid sequences that encode the proteins of the invention. In a preferred embodiment, the nucleic acid encodes a cysteine in positions 64 or 68, or a methionine in position 64 and is at least 60% identical to SEQ ID NO:2, or hybridizes at moderate stringency to SEQ ID NO:2. In a more preferred embodiment, the sequence is SEQ ID NO:2 except that a cysteine is encoded in positions 64 or 68, or a methionine is encoded in position 64. In a most preferred embodiment, the sequence additionally encodes for histidine at position 66 or threonine at position 65. This aspect of the invention includes oligonucleotides that comprise the nucleic acids that encode the variant amino acids at positions 64 or 68.

Another aspect of the invention is a fusion protein comprising the proteins of the invention fused to a His-tag. In a preferred embodiment, the His-tag is fused to the carboxy-terminus of the protein. Any more preferred embodiment, the His-tag is fused to the carboxy side of the histidine 231 via a linker peptide. In a most preferred embodiment, the peptide of SEQ ID NO:3 is fused to the carboxy side of histidine 231. This aspect further includes isolated nucleic acid molecules that encode the fusion protein, and the nucleic acids operably inserted into a vector for replication in cells.

Another aspect of the invention is an expression cassette comprising a coding sequence for the protein of the invention. In a preferred embodiment, the expression cassette comprises the nucleic acid of the invention. In another preferred embodiment, the expression cassette encodes the His-Tag-variant GFP fusion protein of the invention. In more preferred embodiment, the expression cassette comprises regulatory sequences suitable for expression in plant, animal or bacterial cells. In a more preferred embodiment, the expression cassette is operably inserted into a vector for stable transformation of bacterial, plant or animal cells. This aspect of the invention also includes cells transformed with the expression cassette, and plants and animals regenerated from the transformed cells.

BRIEF DESCRIPTION OF THE DRAWINGS

FIG. 4. Graph showing results of refolding studies. Measurements of relative fluorescence taken as mutant and wildtype proteins refold under ambient and low oxygen conditions. Triangles correspond to NSS#1 mutant GFP with ambient $O_2$; diamonds correspond to wild type GFP with ambient $O_2$; circles correspond to NSS#1 mutant GFP with low $O_2$; and squares correspond to wild type GFP with low $O_2$.

FIG. 5. Spectrographs showing the absorbance spectra of wild type and NSS#1 mutant GFPs in low (10 mM Tris, pH 8.0) and high (7 M urea, 10 mM Tris, pH 8.0) ionic strength buffers.

DESCRIPTION OF THE INVENTION

I. Definitions

Various terms relating to the biological molecules of the present invention are used hereinabove and also throughout the specifications and claims. The terms "substantially the same," "percent similarity" and in "percent identity" are defined in detail below.

With reference to nucleic acids of the invention, the term "isolated nucleic acid" is sometimes used. This term, when applied to genomic DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a procaryote or eukaryote. An "isolated nucleic acid molecule" may also comprise a cDNA molecule or a synthetic DNA molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

Nucleic acid sequences and amino acid sequences can be compared using computer programs that align the similar sequences of the nucleic or amino acids thus define the differences. For purposes of this invention, the Blastn and Blastp 2.0 programs provided by the National Center for Biotechnology Information (Altschul et al., 1990, J Mol Biol 215:403–410) using a gapped alignment with default parameters, may be used to determine the level of identity and similarity between nucleic acid sequences and amino acid sequences.

The term "substantially the same" refers to nucleic acid or amino acid sequences having sequence variation that do not materially affect the nature of the protein (i.e. the structure, thermostability characteristics and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, J. Theor. Biol. 119:205). When referring to nucleic acid molecules, "percent identical" refers to the percent of the nucleotides of the subject nucleic acid sequence that have been matched to identical nucleotides by a sequence analysis program.

With respect to protein, the term "isolated go protein" or "isolated and purified protein" is sometimes used herein. This term refers primarily to a protein produced by expression of an isolated nucleic acid in molecule of the invention. Alternatively, this term may refer to a protein which has been sufficiently separated from other proteins with which it would naturally be associated, so as to exist in "substantially pure" form.

The term "substantially pure" refers to a preparation comprising at least 50–60% by weight the compound of interest (e.g., nucleic acid, oligonucleotide, protein, etc.). More preferably, the preparation comprises at least 75% by weight, and most preferably 90–99% by weight, the compound of interest. Purity is measured by methods appropriate for the compound of interest (e.g. chromatographic methods, agarose or polyacrylamide gel electrophoresis, HPLC analysis, and the like).

With respect to antibodies of the invention, the term "immunologically specific" refers to antibodies that bind to one or more epitopes of a protein of interest, but which do not substantially recognize and bind other molecules in a sample containing a mixed population of antigenic biological molecules.

With respect to oligonucleotides, but not limited thereto, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "expression cassette", as used herein, comprises 5' and 3' regulatory regions operably linked to a coding sequence. The coding sequence may be in the sense or antisense orientation with respect to the 5' regulatory region.

The term "promoter region" refers to the transcriptional regulatory regions of a gene, which may be found at the 5' or 3' side of the coding region, or within the coding region, or within introns.

The term "reporter gene" refers to genetic sequences which may be operably linked to a promoter region forming a transgene, such that expression of the reporter gene coding region is regulated by the promoter and expression of the transgene is readily assayed.

The term "vector" refers to a small carrier DNA molecule into which a DNA sequence can be inserted for introduction into a host cell where it will be replicated. An "expression vector" is a specialized vector that contains a gene with the necessary regulatory regions needed for expression in a host cell.

The term "binary vector" refers to vector which carries a modified T-region from the Ti plasmid usually comprising selectable markers for plant transformation between the two boarder regions. A gene of interest can also be placed between these two boarder regions for transfer into a plant cell genome with the assistance of a helper plasmid and the bacterium *Agrobacterium tumefaciens*.

The term "selectable marker gene" refers to a gene product that when expressed confers a selectable phenotype, such as antibiotic resistance, on a transformed cell or plant.

The term "operably linked" or "operably inserted" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

The term "DNA construct" refers to genetic sequence used to transform plants or other organisms (e.g., bacteria, yeast). When transforming plants, these constructs may be administered to plants in a viral or plasmid vector. Other methods of delivery such as Agrobacterium T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1998.

Nucleic acids having the appropriate sequence homology with a nucleic acid molecule may be identified by using hybridization and washing conditions of appropriate stringency. For example, hybridizations may be performed, according to the method of Sambrook et al. (*Molecular Cloning*, Cold Spring Harbor Laboratory (1989)), using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology (Sambrook et al., 1989, supra):

$$T_m = 81.5° C. + 16.6 \text{ Log } [Na+] + 0.41(\% \text{ G+C}) - 0.63(\% \text{ formamide}) - 600/\text{\#bp in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and wash in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and wash in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and wash in 0.1×SSC and 0.5% SDS at 65° C. for 15 minutes.

II. Detailed Description

Figure 2:
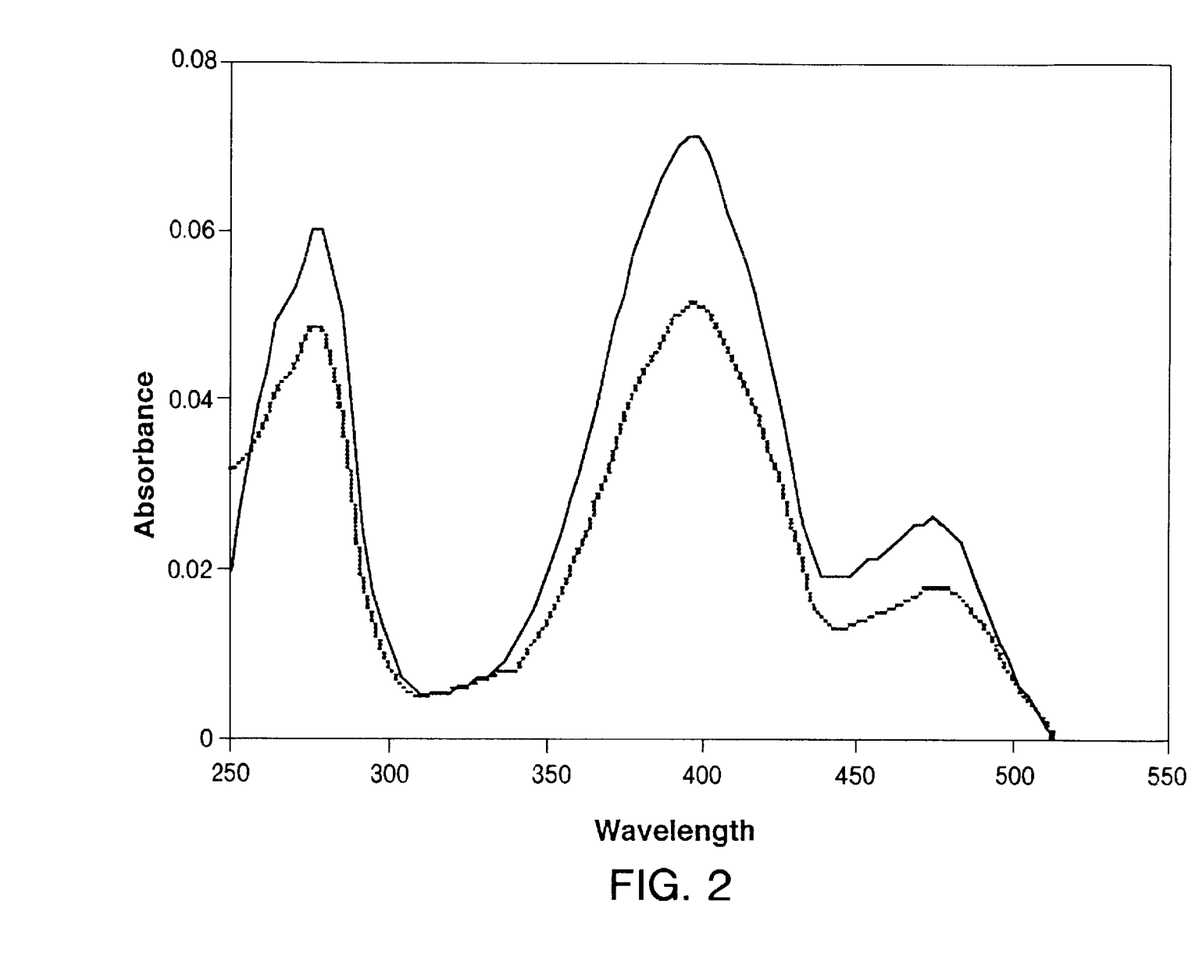
FIG. 2. Absorbance spectra of wild-type GFP and NSS#1 mutant GFP. Solid line, wild type GFP; and broken line, NSS#1mutant GFP.

In accordance with the present invention, a new type of chromophore mutant of the *Aequoria victoria* green fluorescent protein has been isolated by performing an abbreviated DNA shuffling procedure (Stemmer, Nature 370: 389–390, 1994) (modified so as to select after one round of fragmentation and reassembly, without size selection) on the cloned the GFP cDNA. A colony was isolated, which had a form of GFP that displayed unusually rapid fluorescence development and a greater than usual degree of thermotolerance when cells were grown at or above 50° C. The new mutant and wild type GFP could not be distinguished from one another by spectral analysis (FIG. 2). Dynamic whole-cell assays at 37° C. showed a several-fold increase in fluorescence yield. The improvement in fluorescence yield was independent of the promoter used. The advantage was lost upon sonication of the recombinant bacteria expressing the protein. The NSS#1 mutant refolded faster in vitro than the wild type GFP under the conditions of both low oxygen and ambient oxygen. The new mutant had surprising stability as compared to wild type GFP when cells expressing the proteins were taken to temperatures in excess of 50° C. and when isolated protein was heated to 95° C. in 7 M urea.

Figure 1A:
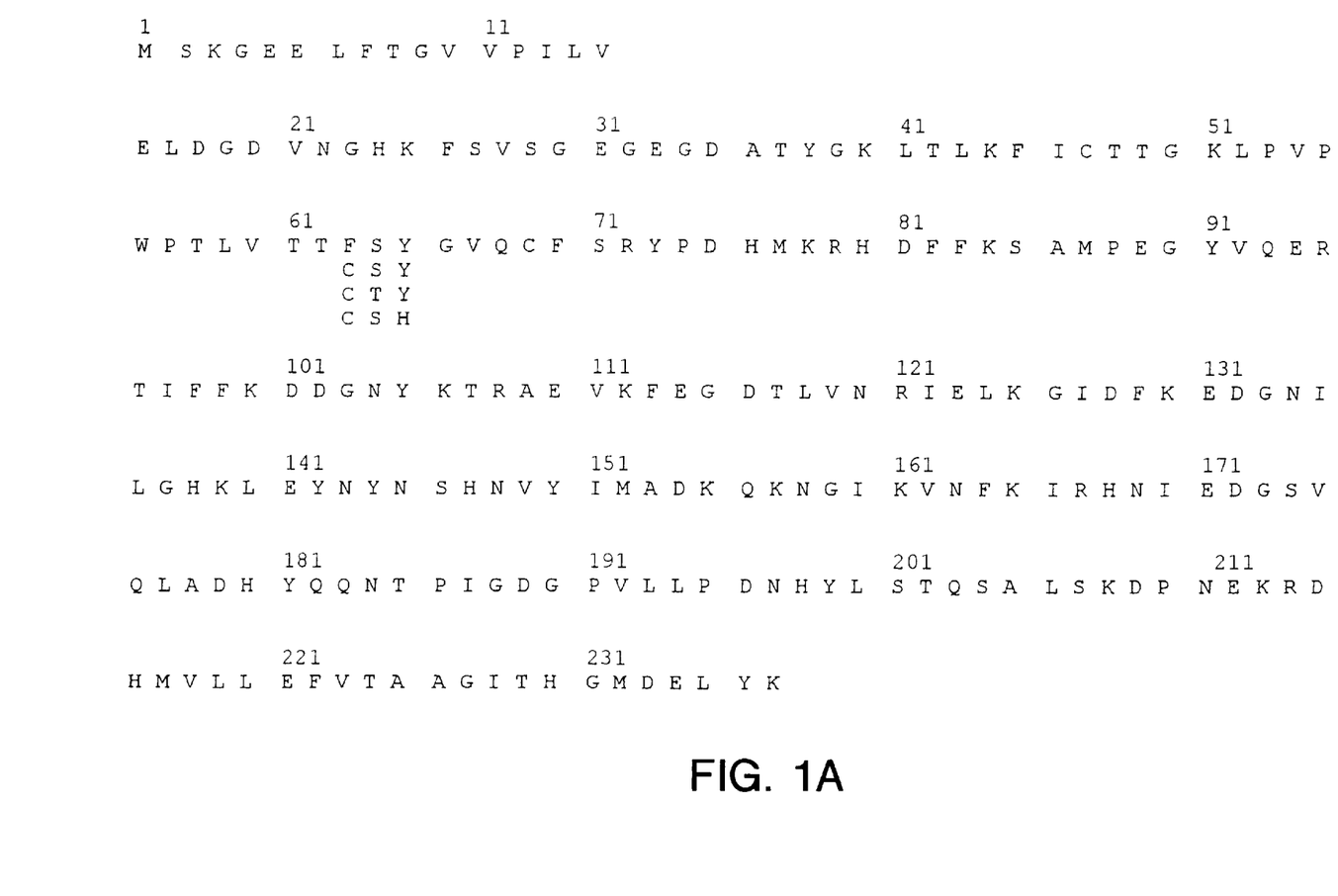
FIG. 1A. Amino acid sequence of the *Aequoria victoria* GFP (SEQ ID NO:1), as found in plasmid pBAD-GFPuv bacterial vector (Clontech, Genbank Accession No. U62637). Numbering of mutants is taken from the methionine, indicated in bold (numbers above the sequence). Mutations resulting in changes in amino acid sequence at position 64–66 are shown below the wild-type sequence.

Sequencing analysis demonstrated that the phenylalanine at position 64 had been substituted by a cysteine (F64C) (FIG. 1A). The benefits of the F64C substitution were observed in both the Y66H (blue) mutant, the S65T (red-shifted) mutant and the cycle 3 mutant (M153T, V163A and F99S; Crameri et al., 1996, Nature Biotech. 14:315–319).

Figure 1B:
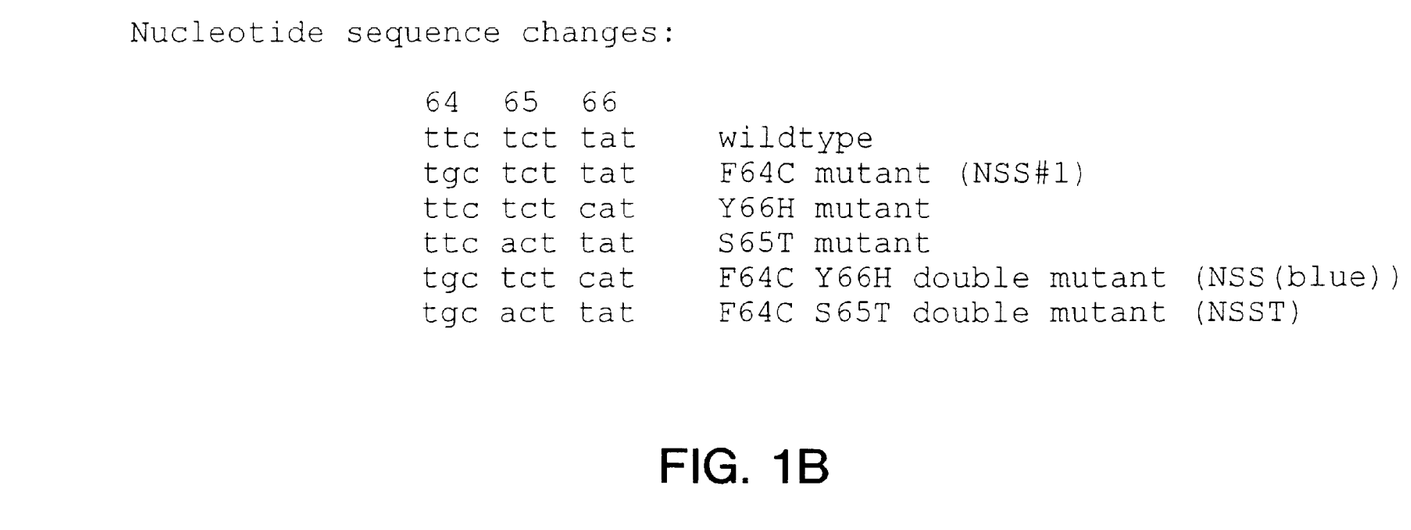
FIG. 1B. Nucleotide sequence changes resulting in amino acid sequence changes at position 64–66 of *Aequoria victoria* GFP.

The F64C single mutant is referred to herein as NSS#1. The F64C/Y66H double mutant is referred to herein as NSS (blue). The F64C/S65T double mutant is referred to herein as NSST (FIG. 1B).

As described in greater detail in the Examples, NSS#1 appears to have a lower oxygen requirement for internal catalysis than does wild type GFP, suggesting that the F64C mutation assists in the internal dehydration /cyclization reaction. The advantage is "portable", as shown by the rapid chromophore development and enhanced thermotolerance displayed by the NSS(blue) and NSST double mutants. The mutant does not appear to be a "folding" mutant (i.e., increased rate of protein folding causing the rapid chromophore development), for reasons described in the Examples. However, no particular mechanism is intended to be excluded as partially or fully contributing to the observed effect.

Without intending to be limited thereby, the following possible mechanisms are proposed to explain the rapid chromophore development of the F64C mutant. It is known that molecular oxygen is required to oxidize the chromophore. In that oxidation reaction, the beta-carbon of $Tyr_{66}$ creates a double bond with the alpha carbon. This occurs immediately adjacent to an aromatic ring. One would predict that this might happen spontaneously, as the aromatic ring might be expected to offer some degree of resonance stabilization to any charged species. However, it appears that molecular oxygen is required. In wild-type GFP, position 64 is occupied by phenylalanine. This residue also would be capable of stabilizing a charged species nearby, if one were present. It is unclear whether phenylalanine affects the oxidation reaction either positively or negatively. However, it is a bulky residue, and might impair access to the developed chromophore ring.

In NSS#1, F64 was replaced with a cysteine. The cysteine is smaller than phenylalanine, and might allow greater access to the chromophore than does the phenylalanine. The substitution of a smaller amino acid, methionine, conferred the same rapid chromophore formation as did the cysteine substitution.

A direct redox effect is another likely explanation of how the cysteine substitution confers the observed rapid chromophore development. Cysteines spontaneously lose their hydrogens and form double bonds in the absence of a strong reducing agent. It is possible that the cysteine in the NSS#1 mutant is active as a proton acceptor, and could abstract one of the hydrogens of the chromophore (at $Tyr_{66}$), leaving a charged species that would be expected to be resonance stabilized by the tyrosine ring. The second loss of a proton would then be much more likely to occur, and might require a lesser requirement for oxygen to become fully oxidized. Other redox effects also may contribute to the rapid chromophore formation.

In addition to the F64C mutation, other mutations have shown, or are expected to show a similar effect, due to size effects or improved redox status in and around the chromophore. For instance, a F64M mutant also exhibits rapid chromophore development under low oxygen conditions, as does a substitution at the carboxyl side of the chromophore. V68C.

In accordance with the invention, there has been discovered a surprising and novel kind of GFP variant, one that conform the chromophore under conditions of low oxygen, as defined in Example 1. In addition to low oxygen chromophore formation, the variants of the invention exhibit the additional trait of rapid chromophore formation with or without low oxygen, as well as a higher stability. This novel assortment of traits describes a new category of GFP variant that is one aspect of the invention.

Several embodiments of the rapid chromophore development are contemplated. The preferred embodiment, the isolated GFP variant forms is chromophore at least 1.25× faster than the isolated nonmutant equivalent GFP (more preferred, at least 1.5×faster, and most preferred at least 1.7×faster) for 0 to 300 minutes in a solution that has been first nitrogen sparged for 20 minutes. In other preferred embodiment, the isolated GFP variant forms and chromophore at least 1.1×faster than the isolated nonmutant equivalent GFP (more preferred, at least 1.2×faster, and most preferred at least 1.25×faster) for 0 to 300 minutes in a solution with ambient oxygen concentration. In another preferred embodiment, the isolated GFP variant forms its chromophore at least 1.5×faster than the isolated nonmutant equivalent GFP (more preferred, at least 2.0×faster, and most preferred at least 2.5×faster) for 0 to 1440 minutes in a solution that has first been nitrogen sparged for 20 minutes. In another preferred embodiment, the isolated GFP variant forms its chromophore at least 1.1×faster than the isolated nonmutant equivalent GFP (more preferred, at least 1.23× faster, and most preferred at least 1.4×faster) for 0 to 1440 minutes in a solution with ambient oxygen concentration.

Several embodiments of the higher fluorescing variant GFP of the invention are contemplated. In a preferred embodiment, the isolated GFP variant fluoresces with identical excitation at least 1.5×brighter than the isolated nonmutant equivalent GFP (more preferred, at least 2.0× brighter, and most preferred, at least 2.5×brighter) after 1440 minutes folding in a solution that has been first nitrogen sparged for 20 minutes. In another preferred embodiment, the isolated GFP variant fluoresces with identical excitation at least 1.1×brighter than the isolated nonmutant equivalent GFP (more preferred, at least 1.23×faster, and most preferred, at least 1.4×faster) after 1440 minutes folding in a solution with an ambient oxygen concentration. For the purposes of the invention, ambient conditions are those which exist in an atmosphere suitable for human life. Nitrogen sparged solution for the purpose of the invention is defined as containing oxygen that is 1 mg/ml, 10% of the oxygen of the solution in ambient conditions (10 mg/ml oxygen).

Several embodiments of the higher stability variant GFP of the invention are contemplated. In a preferred embodiment, the E. coli cells expressing the GFP variant fluoresce with identical excitation at least 1.5×brighter (more preferred, at least 2.0×brighter, and most preferred, at least 2.5×brighter) than E. coli cells expressing a nonmutant equivalent GFP at identical cell density when elevated to a temperature of 42° C. for 10 minutes. In another preferred embodiment, the $$\frac{(480 \text{ nm}/280 \text{ nm in 7M urea, 10 mM Tris, pH 8.0})}{(480 \text{ nm}/280 \text{ nm in 10 mM Tris, pH 8.0})}$$

of the variant GFP is less than 1.60 (more preferred less than 1.40, and most preferred, less than 1.20). In another preferred embodiment, the $$\frac{(390 \text{ nm}/280 \text{ nm in 7M urea, 10 mM Tris, pH 8.0})}{(390 \text{ nm}/280 \text{ nm in 10 mM Tris, pH 8.0})}$$

of the variant GFP is more than 0.9 (most preferred, more than 0.95) than the same for the nonvariant equivalent GFP.

Examples of this novel and surprising category of GFP variant are the F64C, F64M and the V68C mutations. These mutations can be introduced to any "wildtype" GFP in order to create the low oxygen chromophore formation phenotype. Proteins substantially the same as wildtype GFP may also be used. In a preferred embodiment, the GFP proteins are at least 80% (more preferably at least 90% and most preferably at least 95%) similar to the SEQ ID NO:1.

A distinct advantage of the mutations at position 64 is their "portability". The F64C mutation has been successfully combined with the Y66H blue fluorescent mutation (Heim et al., PNAS 91:12501–12504, 1994), the S65T red fluorescence mutation (Heim et al., Nature 373;663–664, 1994) and the cycle3 mutant (Crameri et al., 1996, Nature Biotech. 14:315–319). It is therefore likely that the mechanism of the F64 mutations of the invention is exclusive from those altering fluorescence spectra of the chromophore. It is also likely that the V68C mutation, which also conferred fast chromophore formation at low oxygen concentrations, operates by a similar mechanism to the F64 mutations and is therefore also portable. The variant GFP of the invention therefore encompasses the combination of the mutations of the invention with all other mutations at other positions presently known and to be discovered. Examples of such mutations are well known to those in the art (see Yang et al., 1996, Nature Biotech. 14:1246–1251; Ward, 1998, In *Green Fluorescent Protein: Proterties. Applications and Protocols*, pp 45–75, ed. M. Chalfie and S. Kain, Wiley-Liss)

Nucleic acids that encode the proteins of the invention are also contemplated. These nucleic acids may use a native sequence of GFP to encode the protein or may have altered codon usage to better suit the nucleic acid for expression in heterologous organisms. For example, codons may be selected that will allow the protein to be better expressed in plants (Haseloff et al., 1997, PNAS 94:2122–2127). In a preferred embodiment, the nucleic acids are at least 60% identical (more preferably at least 75%, and most preferably at least 90%) to SEQ ID NO:2. In another preferred embodiment, the nucleic acids hybridize to SEQ ID NO:2 at moderate stringency (more preferably high stringency, and most preferably, very high stringency). oligonucleodides that are at least 15 nucleotides in length, (more preferably 20 nucleotides and most preferably 30 nucleotides) that comprise the variant region of the nucleotides of the invention are also presented.

The rapid greening mutants of the present invention may be used to advantage for a variety of applications in in vitro, in situ, and in vivo bioluminescent labeling, especially where low oxygen would limit chromophore development in other GFPs. The rapidly greening mutants can be used for any labeling application in which GFP is currently used. In addition, it may be used to particular advantage as an in situ marker of low oxygen status in cells and tissues. (Note, fully oxygen saturated water contains about 10 mg/L. Confluent bacterial colonies are expected to be significantly lower in oxygen content). Some examples of instances in which oxygen status is important are discussed below.

The low oxygen GFP variant of the invention shows a surprising stability in harsh environments that will be useful in many in vitro and in vivo application of GFP. Since wildtype GFP changes its spectra in response to pH shifts, the presence of organic solvents, salt concentration, among others, an inaccuracy is introduced into applications that require the quantification of the GFP fluorescence signal. If a GFP an molecule undergoes a spectral shift in response to the environment, a misleading fluorescence output signal can result leading to the underestimation or overestimation of GFP molecules present. The variant GFPs of the invention may be used in situations where wild type GFP would not be stable, i.e. high ionic strength buffers and/or high temperature. This enhanced stability may be particularly useful when expressing the GFP in halophytes, thermophytes, and in organelles with varying salt and membrane compositions.

The mutant/variant GFPs of the invention will be useful as a detectable substance in any application in food production where anaerobic or alcoholic fermentation is utilized, including manufacturing of cheese, yogurt, pickles and beer, to name a few. Also included are alcohol fermentations other than ethanol, such as methanol for fuel production, or glycerol.

As another example, in municipal waste treatment sewage is treated microbially, and the monitoring of oxygen in such processes is critical because microbial degradation is slowed in the absence of oxygen. Most of the actual digestion in such systems takes place in ill-defined microbial films. This would be a useful situation in which to employ an engineered combination of digestive enzymes and GFP, to give an immediate indication of whether the enzyme being tested confers a degradative advantage under low oxygen conditions.

As an example in agriculture, nitrogen fixation is accomplished under anaerobic conditions by nitrogen-fixing bacteria in specialized bodies called heterocysts. Heterocysts are such a strongly reducing environment that wildtype GFP does not remain fluorescent, but the mutant GFPs of the present invention should.

As another example, a great deal of soil microbiology takes place under poorly oxidizing conditions. The GFPs of the present invention could be used to monitor microbial processes in soils, whereas wild-type GFPs are not well suited for this purpose.

Toxic waste cleanup is often done under low oxygen conditions. The GFPs of the present invention may be used to advantage to monitor activity of detoxifying microbial agents.

The following examples are provided to describe the invention in greater detail. They are intended to illustrate, not to limit, the invention.

EXAMPLE I

Improved Low Oxygen Chromophore Formation of Mutant GFP

The F64C mutant (NSS#1) has a brightness advantage over wild-type GFP on both agar plates and in LB medium when expressed by otherwise identical bacteria containing otherwise identical plasmids. To determine if oxygen affinity plays a role in the "quick brightening" effect displayed by NSS#1, an experiment was performed in which matched cultures and sonicates were prepared, and access to oxygen was impaired by encasement in polyacrylamide.

Materials and Methods

Four matched pairs of bacterial cultures or sonicates were prepared. The matched cultures/sonicates were recombinant bacteria grown in LB/Amp expressing either NSS#1 or wild type GFP. Matched cultures were pelleted by centrifugation. Four treatments were performed.

In pair #1, maturation of the GFP was allowed to occur under reduced oxygen tension in whole bacteria. The two cultures were centrifuged and immediately encased in acrylamide, without prolonged exposure to ambient oxygen. The protein was allowed to mature in situ for 48 hours at room temperature at the bottom of a pair of 50 ml Falcon tubes, under 10 ml of acrylamide supplemented with kanamycin and azide.

In pair #2, GFP maturation was designed to take place outside the bacterial environment and within a low oxygen environment, without further protein synthesis. The bacteria were sonicated and centrifuged, and the soluble contents were resuspended from the cell paste in 5 ml of 20% acrylamide (containing kanamycin and azide) and polymerized. The acrylamide plug was placed underneath a second, larger acrylamide plug (10 ml) to further inhibit oxygen diffusion.

In pair #3, maturation was allowed to take place outside the bacteria that produced the GFP with continuous exposure to ambient oxygen at room temperature. The bacteria were centrifuged, sonicated, and the debris re-centrifuged. The soluble fractions were allowed to mature within opened tubes in the absence of protein synthesis.

In pair #4, GFP matured within intact bacteria exposed to room air. Bacteria were pelleted and exposed to ambient oxygen for 48 hours in the presence of kanamycin and azide. Thereafter they were sonicated, resuspended and encased in acrylamide.

All cultures were grown overnight at 37° C. with equal agitation. Cultures containing NSS#1 were brighter than wild-type cultures at the end of the overnight incubation; however the cultures were matched for OD600 (turbidity measurement) prior to the treatments. All cell pellets or sonicates, if resuspended, were treated with an excess of both kanamycin and azide in order to inhibit protein synthesis. Excess kanamycin and azide were also used in acrylamide encasement procedures.

Acrylamide encasement was used to eliminate any oxygen present in the sonicates before polymerization as well as to create a barrier to oxygen diffusion following completion of polymerization. To accomplish this, 10 ml of 20% acrylamide was polymerized directly on top of solid bacterial pellets, while 5 ml of the same solution was mixed with any pre-centrifuged sonicates and completely polymerized before an additional layer of acrylamide was polymerized directly on top of the sonicate-containing plug.

Results

Pair #1—Whole bacteria, reduced oxygen. The NSS#1 containing bacteria were about 5-fold brighter than the wild-type bacteria at the outset of the experiment. After 48 hours, NSS#1 continued to brighten, while the wild-type bacteria appeared less bright. Over the next two weeks, NSS#1 continued to get brighter, until the strong green tint in the bacterial pellet was visible by daylight. The wild-type bacteria became progressively less bright, until fluorescence was difficult to detect with UV light.

Pair #2—Sonicates encased in acrylamide. At the outset of the experiment, the NSS#1-containing bacteria were about 3-fold brighter than the wild-type bacteria. The respective brightness of the two encased sonicates did not change appreciably over the 48 hour incubation period. However, after one year of storage, the wild-type sample continued to brighten, until the two samples were essentially indistinguishable.

Pair #3—Maturation outside of bacteria with exposure to air. At the beginning of the experiment, the NSS#1 bacteria were about 5-fold brighter than the wild-type bacteria. Immediately after sonication, the NSS#1 sonicate was much brighter than the wild-type sonicate. However, after 48 hours of exposure to ambient air, the two sonicates were indistinguishable.

Pair #4—Pellets allowed 48 hours exposure to air, followed by sonication and encasement in acrylamide. At the outset of the experiment, the NSS#1 bacteria were about 5-fold brighter than the wild-type bacteria. 48 hours of room temperature air exposure did not appear to alter the relative brightness of the respective cultures, though both culture became brighter during that time. After sonication and encasement in acrylamide, the comparative brightness remained essentially unchanged. However, after one year of storage, the wild-type sample became comparatively brighter, and was essentially indistinguishable from the NSS#1 sample. Both samples became brighter during the one-year period.

The foregoing experiments distinguished the nature of the NSS#1 advantage. Others have reported "folding mutants" that presumably form the intricate "Beta can" structure of mature GFP more readily than wild-type GFP. One such mutation is F64L (Cormack et al., Gene 173: 33–38, 1996). However, if such a mechanism were occurring with the F64C mutant, one would expect to see the same relative brightening in intact cells as seen in sonicates. This is not the case. In intact bacteria, NSS#1 continued to brighten, and wild-type bacteria never "caught up." In contrast, wild-type brightness in sonicates became equivalent to NSS#1 brightness over extended periods of time. This difference suggests that the environment of the intact bacteria, which is believed to be a strongly reducing environment, affects the mechanism by which the NSS#1 chromophore is formed. One possible mechanism may involve an improved redox potential for chromophore formation due to the substitution of cysteine for phenylalanine immediately adjacent to the chromophore.

EXAMPLE II

Improvement in Fluorescence Yield of Mutant GFP

Materials and Methods

A dynamic assay to determine fluorescence yield of NSS#1 to wild type GFP was performed. Inducible GFP wild-type and NSS#1 mutant expression vectors were constructed, using the pBADGFP-uv vector from Clontech. The carboxy-terminal ends of the expression vector were modified to include a his(6) tag for purification purposes. This his(6) tag is separated from the Beta-can GFP structure by introduction of a cloning site (Kpn I) that places a serine-valine-proline upstream of a flexible linker (ser-gly-gly-gly SEQ ID NO:3, residues 4–7). From His231, the new sequence creates Ser232, Val233, Pro234, Ser235, Gly236, Gly237, Gly238, His(6), Stop (SEQ ID NO:3). This created a GFP of 244 residues. The spectral characteristics of GFP appeared to be unchanged by the modifications.

For the experiment, DH5-α E. coli were grown overnight in LB supplemented with 50 mg/liter ampicillin and diluted to an OD at 600 nm (OD600) of 0.3, where log-phase growth was allowed to continue. After 1 hour, protein expression was induced by the addition of 0.2% (final concentration) arabinose. All growth took place at 37° C. in 1 L fermentation flasks with vigorous shaking. Samples of fermentation broth were taken at various time points and measured both for OD600 with a Spectronic Genosys 2 spectrophotometer, while relative fluorescence units were determined with a Turner Designs TD700 model fluorometer set to excite in the UV range. All samples required dilution by 10 mm tris to remain within the linear ranges of the instruments.

After each sample was measured directly from the fermentation broth, it was placed in an ice bath for six hours before a second series of readings were taken. This was done to test the hypothesis that NSS#1 was a "folding mutant", and thus would be able to reach full fluorescence without the aid of such a cooling step. Were this hypothesis correct, NSS#1 would not increase its fluorescence yield after such a treatment.

Results

While not limiting the mechanism of the invention, the data indicate that NSS#1 is not a "folding mutant". Both wt and NSS#1 greatly increased their fluorescence outputs in response to a cooling step. Both averaged a measured increase of about three fold, indicating that NSS#1 did not fold more completely than the wt during the 37° C. growth phase.

The data also show that, in contrast to observations reported for the Cycle3 mutant, bacteria expressing NSS#1 do not grow significantly more quickly than bacteria expressing wt. Thus, bacteria expressing NSS#1 were not brighter than those expressing wt merely because there were more bacteria per volume. In fact, the OD600s tended to stay within 10% of each other (the wt GFP often displaying higher OD600) throughout the course of this experiment. This suggests that NSS#1 is not significantly less toxic than wt GFP, unlike Cycle3.

Figure 3:
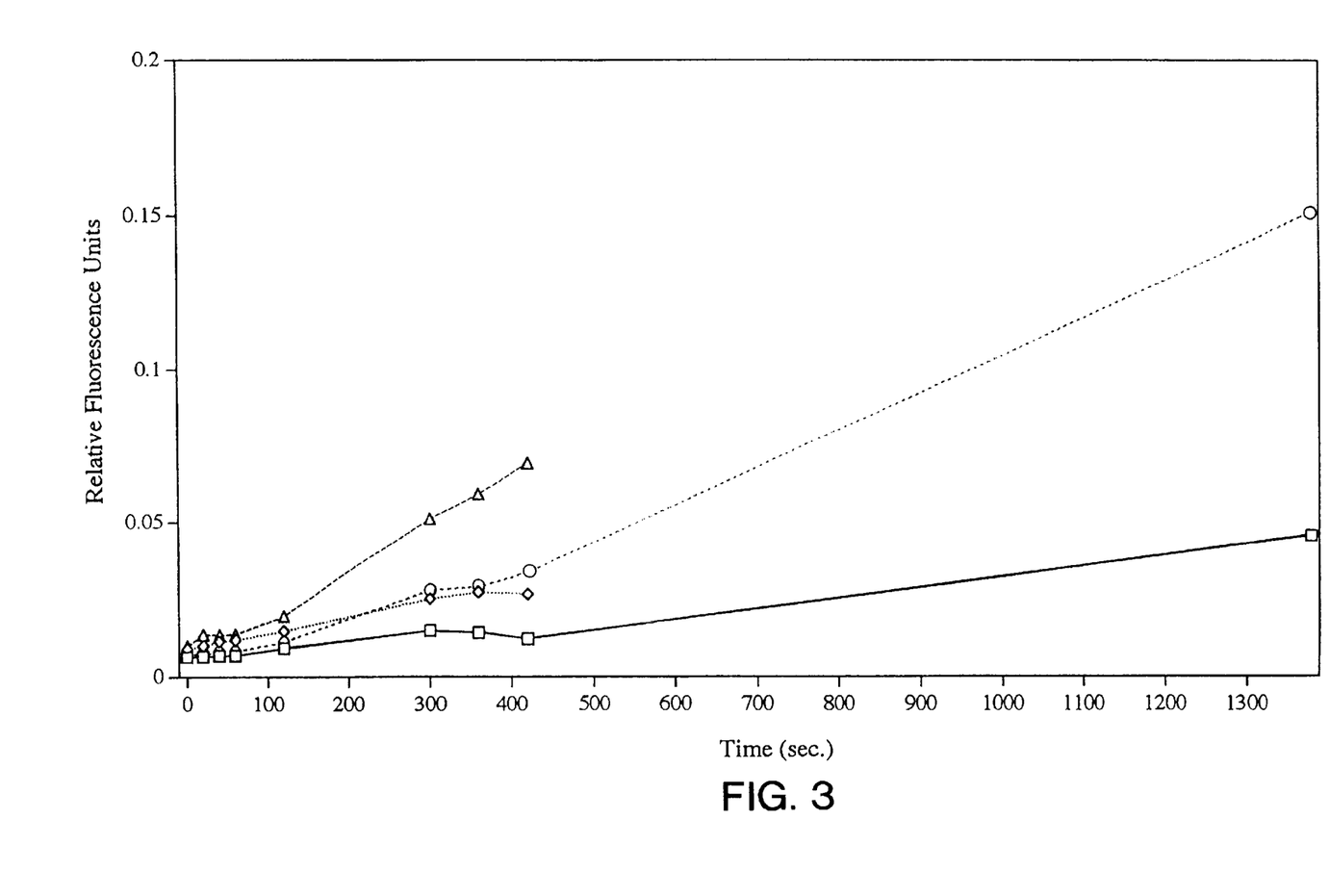
FIG. 3. Graph showing results of dynamic assay of whole cell fluorescence in *E. coli* expressing wild-type GFP or NSS#1 mutant GFP. Measurements were taken before and after 6 hours of incubation at 0° C. Squares correspond to wild type GFP before incubation; diamonds correspond to wild type GFP after incubation; circles correspond to NSS#1 mutant GFP before incubation; and triangles correspond to NSS#1 mutant GFP after incubation.

Direct comparisons of fluorescence yield gave variable ratios between NSS#1 and wt throughout the experiment (FIG. 3). Once adjusted for background fluorescence from both media components and bacterial metabolites, the whole-cell brightness advantage of NSS#1 ranged between 0.2 fold and 5.8 fold. But by 5 hours post-induction, the NSS#1 cell pellets displayed stronger fluorescence than almost any other GFP previously observed, while the wt pellet was just beginning to display fluorescence detectable by the naked eye. However, after a freeze-thaw step and subsequent centrifugation, (commonly employed to liberate recombinant protein), the NSS#1 supernatant demonstrated a 35-fold improvement over the wt supernatant.

Differences in solubility could not account for these results. The residual cell pellets were vastly different in appearance: the wt pellet had a characteristic tan pigmentation with a moderate level of GFP fluorescence, while the NSS#1 residual pellet resembled chopped spinach, with GFP fluorescence vastly brighter than any other GFP observed, with the possible exception of Cycle3. The final whole-cell GFP concentrations, as determined by the Turner TD-700 instrument, were calculated as 19 mg/L of WT GFP, and 75 mg/L NSS#1 with a six-hour incubation on ice. NSS#1 has a wild-type excitation spectra and emission profile.

EXAMPLE III

NSS#1 is an Oxidation Mutant: Microaerobic Refolding and Real-time Fluorescence Assay Inclusion body apo-GFPs were extracted from insoluble cell paste from engineered bacteria overexpressing either wt GFP or the NSS#1 mutant and allowed to refold either in a buffer extensively sparged with N2 to eliminate $O_2$ or in the same buffer at ambient $O_2$ tension (see Reid and Flynn, 1997, Biochemistry 36:6786–6791). The fluorescence acquisition of the refolding proteins followed established patterns when the reactions occurred at ambient $O_2$ pressure; however, reactions performed at a much reduced $O_2$ tension were dramatically impaired. The wt protein displayed approximately 7.3% of the control levels of fluorescence. In contrast, the NSS#1 mutant displayed 14+% of its control values toward the later portions of the assay, confirming that NSS#1 is an oxidation mutant. At all points past 2.5 hours in this assay, NSS#1 appeared dramatically brighter than the wt GFP, regardless of the conditions imposed.

Methods

Preparation of apo-GFPs. Various GFPs bearing a carboxy terminal hexahistidine affinity tag were overexpressed in E. coli DH5-alpha from an arabinose-induced vector system at a non-permissive temperature (3° C.) with vigorous aeration in a modified LB media supplemented with 200 ug/ ml ampicillin and 0.2% arabinose. Bacteria were harvested by centrifugation and washed by resuspension in 10 mM Tris, pH 8.0, and centrifuged again. The dry pellets were directly sonicated while remaining on ice until the pellet appeared liquified. The lysate was then extracted with "lysis buffer" (200 mM NaCl and 50 mM Tris, pH 8.0) and centrifuged again. The supernatant was discarded and the pellet was examined for evidence of fluorescence.

The wildtype GFP pellet did not exhibit the characteristic fluorescence of GFP, but the NSS#1 pellet did. The sonification procedure was repeated an additional two times. The resulting cellular paste was resuspended in "resuspension buffer" (35 mM KCl, 2 mM $MgCl_2$, 50 mM Tris pH 7.5 and 20 mM mercaptoethanol) and immediately frozen at −20° C. For assay purposes, stored apo-GFP was thawed at 42° C., vortexed and used immediately. The resuspended paste was returned to storage at −20° C. immediately. 200 µl of resuspended paste was mixed with 1400 µl "Denaturing solution" (8M urea, 20 mM mercapitoethanol, 10 mM Tris pH 8.0) and allowed to incubate at room temperature for 15 minutes. It was then centrifuged at maximum rpm in a Heraeus Biofuge for 30 minutes. The urea supernatant was retained for further evaluation.

Assay for development of GFP. Urea supernatants bearing apo-GFPs were diluted 100×into resuspension buffer, typically vortexed, aliquoted into 100 mm×13 mm fluorescence tubes and placed directly into a Turner Designs TD-700 fluorometer. Readings were taken as soon as they stabilized. In this experiment, half of the resuspension buffer was extensively sparged with $N_2$ gas for 20 minutes, overlaid with 2 ml machine oil, and then aliquoted to 50 ml Falcon tubes to which an oil overlay was also added. Apo-GFPs were then added to these tubes.

Results

Figure 4:
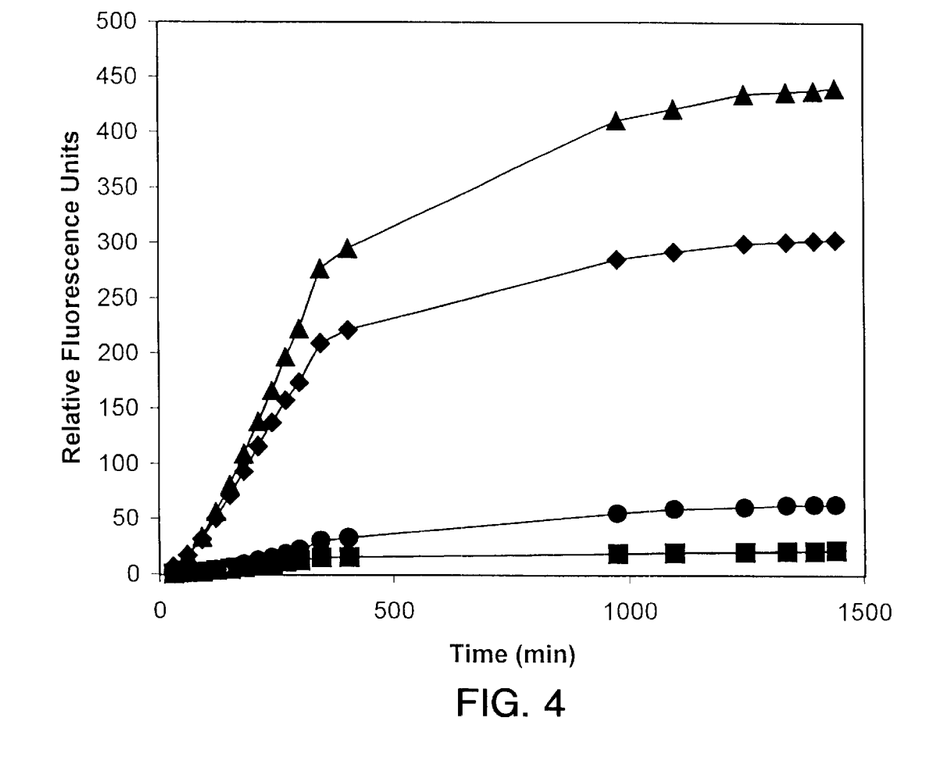

All tubes gained fluorescence as maturation progressed (FIG. 4). The mutant NSS#1 displayed more fluorescence than its wildtype pair regardless of whether or not $O_2$ was at ambient or restricted levels at nearly all time points. At 24 hours after folding initiation, NSS#1 displayed nearly twice as much $O_2$-restricted fluorescence relative to its unrestricted control (NSS#1 at ambient $O_2$) than did the wildtype in the same comparison (wt at ambient $O_2$). Furthermore, the NSS#1 mutant displayed nearly three times as much fluorescence when $O_2$ was restricted than did the $O_2$ restricted wildtype. The final comparison of fluorescence yield after 24 hours of incubation at room temperature were 7.4% of control value (ambient $O_2$) for low $O_2$ wildtype GFP, and 14.3% of control (ambient $O_2$) for low $O_2$ NSS#1 GFP.

EXAMPLE VI

Unusual Stability of NSS#1 in Extreme Environments

Figure 5A:
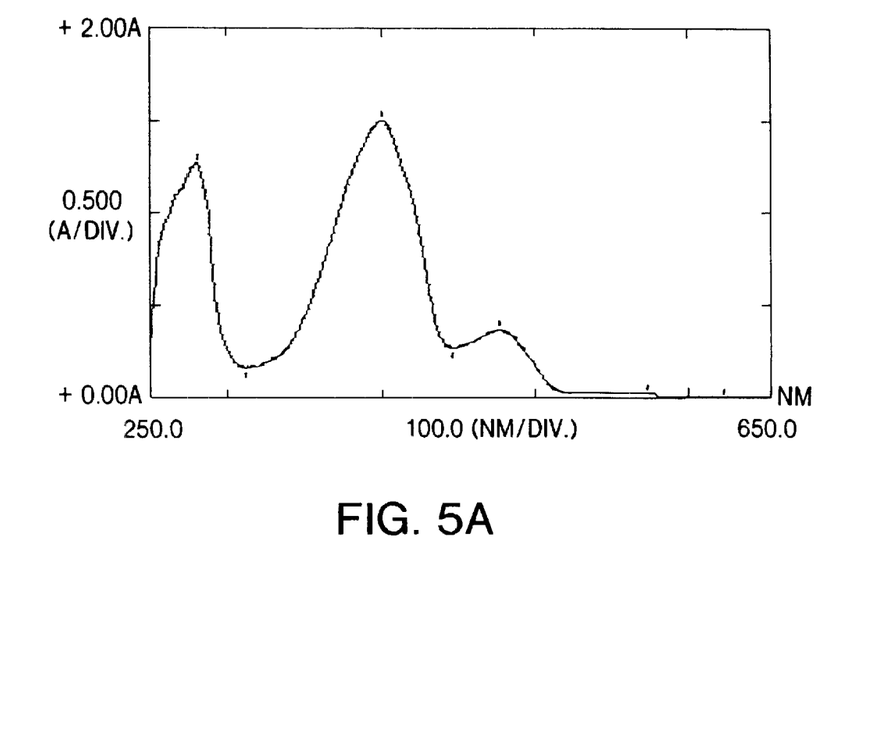
FIG. 5A, wild type GFP in low ionic strength buffer.
Figure 5B:
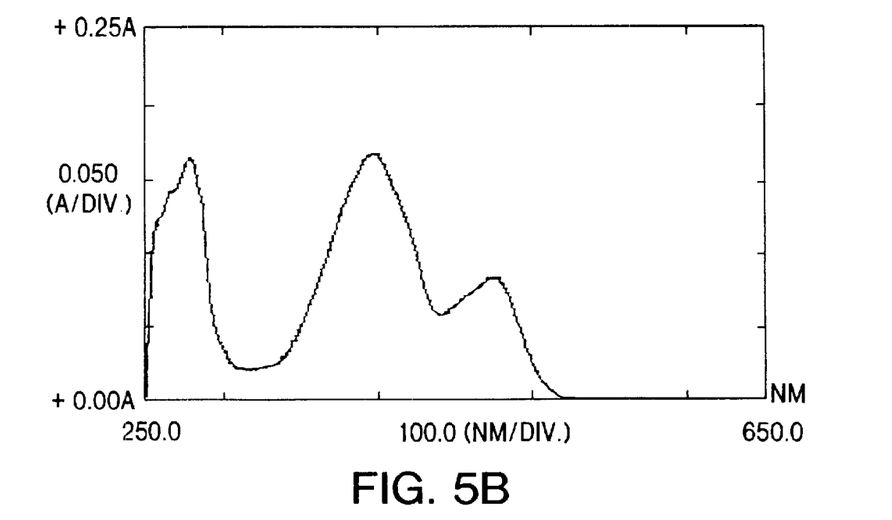
FIG. 5B, wild type GFP in high ionic strength buffer.
Figure 5C:
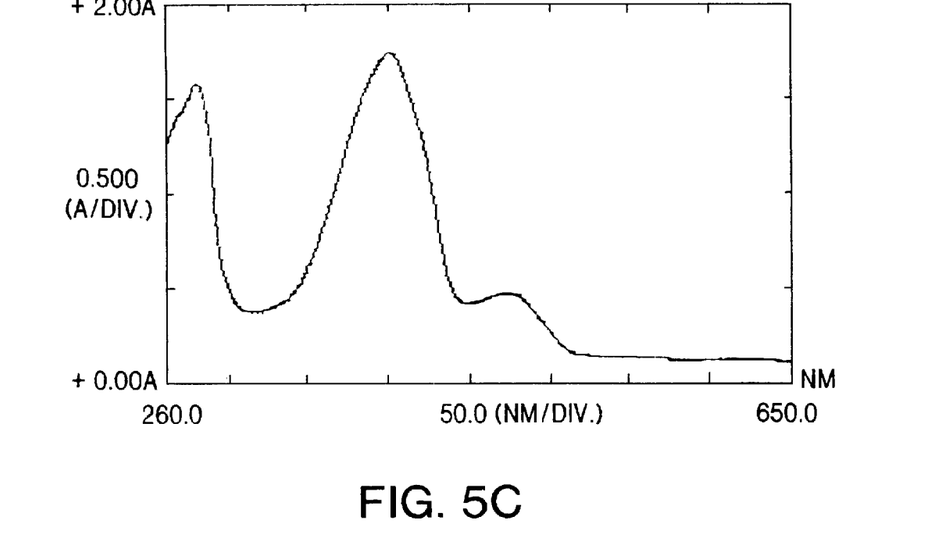
FIG. 5C, NSS#1 mutant GFP in low ionic strength buffer.
Figure 5D:
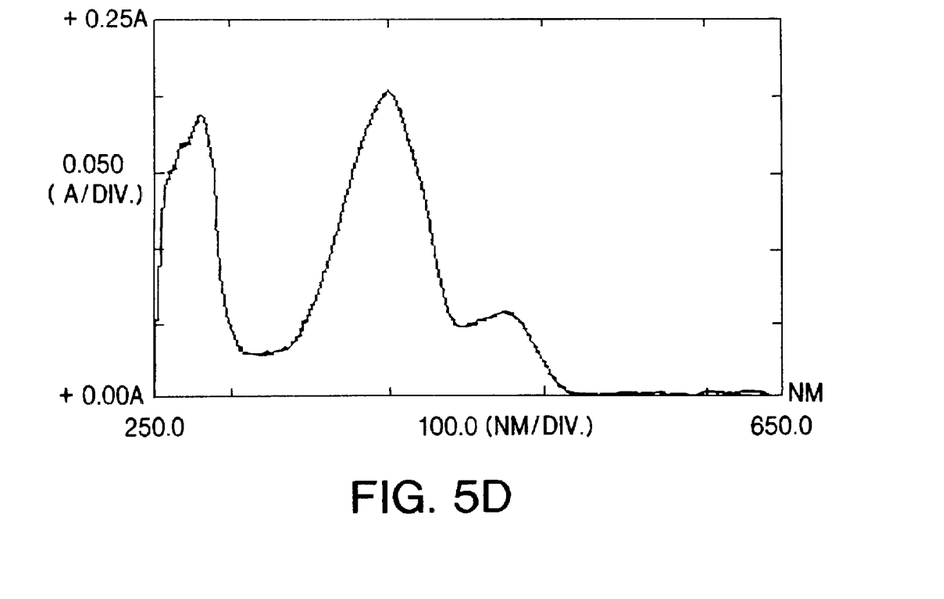
FIG. 5D, NSS#1 mutant in high ionic strength buffer.

Chemical stability. Two aliquots of purified GFP proteins were first scanned in a weakly ionic buffer (10 mM Tris, pH 8.0) and the diluted into a very strongly ionic buffer (7 M urea, 10 mM Tris, pH 8.0). The NSS#1 GFP did not suffer spectral perturbations in response to environmental conditions, unlike wildtype GFP. The wildtype GFP gained absorbance in the 470 nm range, and lost absorbance in the 390 nm range in response to 7 M urea (FIGS. 5A & B). The mutant NSS#1 did not gain or lose significant absorbance in either the UV (about 390 nm) or blue (about 480 nm) ranges in response to the strongly ionic environment (FIGS. 5C & 5D). These absorbance changes are most evident when the 280 nm peak is used as a reference (Table 1).

TABLE 1

Peak absorbencies of wild type GFP and NSS#1 mutant GFP in low and high ionic buffers.

| Wavelength of Peak (nm) | WT without urea | WT with 7 M urea | NSS#1 without urea | NSS#1 with 7 M urea |
|---|---|---|---|---|
| 472.5–476 | 0.374 | 0.080 | 0.473 | 0.057 |
| 397–399 | 1.499 | 0.166 | 1.736 | 0.202 |
| 277.5–279 | 1.269 | 0.164 | 1.571 | 0.186 |
| 480 nm: 280 nm | 0.295 | 0.488 | 0.301 | 0.306 |
| 390 nm: 280 nm | 1.181 | 1.012 | 1.105 | 1.086 |

Thermal stability. The NSS#1 mutant GFP also shows surprising stability at higher temperatures that the wild type GFP. When GFPs are denatured at 95° C. in 7 M urea, the wild type GFP loses its fluorescence in about 5 minutes, while the NSS#1 mutant GFP retains its fluorescence several minutes longer. When cells expressing wild type or NSS#1 mutant GFP are elevated to temperature in excess of 50° C., the NSS#1 mutant GFP cells are noticeably more fluorescent than the wild type cells. Finally, when the two GFPs are expressed in bacteria at 42° C., the wild type GFP is insoluble and non-fluorescent while the NSS#1 mutant GFP is soluble and fluorescent. These data indicate that the mutant's beta-can configuration is more stable than the wild type GFP beta-can configuration under harsh environmental conditions.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

SEQUENCE LISTING

<160> NUMBER OF SEQ ID NOS: 3

<210> SEQ ID NO 1
<211> LENGTH: 238
<212> TYPE: PRT
<213> ORGANISM: Aequorea victoria
<300> PUBLICATION INFORMATION:
<301> AUTHORS: Prasher, D.C. et al.
<302> TITLE: Primary structure of the Aequorea victorea green-f
<303> JOURNAL: Gene
<304> VOLUME: 111
<306> PAGES: 229-233
<307> DATE: 1992-01-01
<308> DATABASE ACCESSION NUMBER: Genbank M62653
<309> DATABASE ENTRY DATE: 1993-04-26

<400> SEQUENCE: 1

Met Ser Lys Gly Glu Glu Leu Phe Thr Gly V al Val Pro Ile Leu Val
 1               5                  10                  15

Glu Leu Asp Gly Asp Val Asn Gly His Lys P he Ser Val Ser Gly Glu
            20                  25                  30

Gly Glu Gly Asp Ala Thr Tyr Gly Lys Leu T hr Leu Lys Phe Ile Cys
        35                  40                  45

-continued

```
Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr His Gly Met Asp Glu Leu Tyr Lys
225                 230                 235
```

<210> SEQ ID NO 2
<211> LENGTH: 966
<212> TYPE: DNA
<213> ORGANISM: Aequorea victoria
<300> PUBLICATION INFORMATION:
<301> AUTHORS: Prasher et al.
<302> TITLE: Primary structure of the Aequorea victoria green-f
<303> JOURNAL: Gene
<304> VOLUME: 111
<306> PAGES: 229-233
<307> DATE: 1992-01-01
<308> DATABASE ACCESSION NUMBER: Genbank M62653
<309> DATABASE ENTRY DATE: 1993-04-26

<400> SEQUENCE: 2

```
tacacacgaa taaaagataa caaagatgag taaaggagaa gaactttttca c tggagttgt    60 cccaattctt gttgaattag atggtgatgt taatgggcac aaattttctg t cagtggaga   120 gggtgaaggt gatgcaacat acggaaaact taccettaaa tttatttgca c tactggaaa   180 actacctgtt ccatggccaa cacttgtcac tactttctct tatggtgttc a atgcttttc   240 aagataccca gatcatatga acagcatga cttttttcaag agtgccatgc c cgaaggtta   300 tgtacaggaa agaactatat ttttcaaaga tgacgggaac tacaagacac g tgctgaagt   360 caagtttgaa ggtgatacce ttgttaatag aatcgagtta aaaggtattg a ttttaaaga   420 agatggaaac attcttggac acaaattgga atacaactat aactcacaca a tgtatacat   480 catggcagac aaacaaaaga atggaatcaa agttaacttc aaaattagac a caacattga   540 agatggaagc gttcaactag cagaccatta tcaacaaaat actccaattg g cgatggccc   600 tgtccttta ccagacaacc attacctgtc cacacaatct gccctttcga a agatcccaa   660 cgaaaagaga gaccacatgg tccttcttga gtttgtaaca gctgctggga t tacacatgg   720 catggatgaa ctatacaaat aaatgtccag acttccaatt gacactaaag t gtccgaaca   780
```

―continued

```
attactaaaa tctcagggtt cctggttaaa ttcaggctga gatattattt a tatatttat    840 agattcatta aaattgtatg aataatttat tgatgttatt gatagaggtt a ttttcttat    900 taaacaggct acttggagtg tattcttaat tctatattaa ttacaatttg a tttgacttg    960 ctcaaa                                                                966
```

<210> SEQ ID NO 3
<211> LENGTH: 13
<212> TYPE: PRT
<213> ORGANISM: Artificial Sequence
<220> FEATURE:
<223> OTHER INFORMATION: synthetic sequence

<400> SEQUENCE: 3

```
Ser Val Pro Ser Gly Gly Gly His His His H is His His
 1               5                   10
```

What is claimed:

1. A green fluorescent protein (GFP) variant exhibiting, under oxygen concentration that is equal or lower than atmospheric, rapid chromophore development as compared with a wild-type GFP of SEQ ID NO: 1, the GFP variant consisting of a GFP variant with one mutation in the sequence of SEQ ID NO: 1 and wherein the GFP variant is selected from the group consisting of F64C, F64M and V68C.

2. A GFP variant of claim 1 which, under lower oxygen concentration, develops fluorescence more rapidly than wild-type GFP of SEQ ID NO: 1.

3. The GFP variant of claim 1 which, under atmospheric oxygen concentration, develops fluorescence more rapidly than the wild-type GFP of SEQ ID NO: 1.

4. The GFP variant of claim 3, which is more stable above 50° C. than the wild-type GFP of SEQ ID NO: 1.

5. A fusion protein that comprises the GFP variant of claim 1 and a His-tag.

6. The fusion protein of claim 5, in which the His-tag is fused to the carboxy-terminus of the protein via a linker peptide.

7. The fusion protein of claim 5, in which the His-tag is fused to the carboxy side of the histidine residue corresponding to position 231 of SEQ ID NO: 1.

8. The fusion protein, in which the sequence corresponding to SEQ ID NO:3 is fused to the carboxy side of the histidine residue corresponding to position 231 of SEQ ID NO:1.

* * * * *

UNITED STATES PATENT AND TRADEMARK OFFICE
CERTIFICATE OF CORRECTION

PATENT NO.   : 6,414,119 B1
DATED        : July 2, 2002
INVENTOR(S)  : Hugh Fisher It is certified that error appears in the above-identified patent and that said Letters Patent is hereby corrected as shown below:

<u>Column 2,</u>
Line 11, please delete "it" before "oxygen".

<u>Column 8,</u>
Line 3, please delete "conform" and insert -- can form --.

<u>Column 20,</u>
Line 22, please delete "50ºC." and insert -- 50ºC --.

Signed and Sealed this

Eleventh Day of November, 2003

JAMES E. ROGAN
*Director of the United States Patent and Trademark Office*